United States Patent [19]
Shimazu et al.

[11] Patent Number: 6,113,552
[45] Date of Patent: Sep. 5, 2000

[54] PAIN MEASUREMENT SYSTEM AND METHOD

[75] Inventors: Hideaki Shimazu, Tokyo; Kuniko Sagara, Koshigaya, both of Japan

[73] Assignee: International Medical Device Partners, Inc., Las Vegas, Nev.

[21] Appl. No.: 09/193,945

[22] Filed: Nov. 18, 1998

[51] Int. Cl.[7] .................................................. A61B 5/00
[52] U.S. Cl. ........................................................ 600/557
[58] Field of Search .................................. 600/552, 553, 600/554, 555, 557

[56] References Cited

U.S. PATENT DOCUMENTS

| | | | |
|---|---|---|---|
| 4,641,661 | 2/1987 | Kalarickal | 128/744 |
| 4,763,666 | 8/1988 | Strian et al. | 128/742 |
| 5,022,407 | 6/1991 | Horch et al. | 600/557 |
| 5,191,896 | 3/1993 | Gafni et al. | 128/742 |
| 5,220,921 | 6/1993 | Ferris et al. | 600/557 |
| 5,363,859 | 11/1994 | Tuckett et al. | 128/739 |
| 5,381,805 | 1/1995 | Tuckett et al. | 600/557 |
| 5,522,386 | 6/1996 | Lerner | 128/630 |
| 5,533,514 | 7/1996 | Lavigne et al. | 128/744 |
| 5,592,947 | 1/1997 | Lavigne et al. | 128/744 |
| 5,806,522 | 9/1998 | Katims | 128/741 |

*Primary Examiner*—Max Hindenburg
*Attorney, Agent, or Firm*—Fulwider Patton Lee & Utecht, LLP

[57] ABSTRACT

Disclosed is a pain measurement system and method that make possible the quantitative measurement of human clinical pain. The perception of the pain generated by the subject's source of preexisting pain is compared with a pseudo pain feeling which is produced by a gradual change in an electric stimulus generated by the system. This device measures the point at which the subject's perception of actual pain approximates the intensity of the pseudo pain feeling generated by the system. In this way the magnitude of the source of pain [x] is estimated quantitatively. The minimum perception level of a subject is also determined and a ratio of current level for actual pain to current level for minimum perception level is taken to quantify the pain.

21 Claims, 7 Drawing Sheets

PAIN MEASUREMENT SYSTEM AND METHOD

BACKGROUND OF THE INVENTION

The invention relates generally to physiological measurement systems, and more particularly, to a system and method for measuring pain in a patient.

Pain can be described as an unpleasant physical sensation experienced in response to injury, disease, or other negative stimuli. Although the experience of pain is extremely subjective, there is clearly a sensuous difference in pain felt by different people in different circumstances. Pain is an individual's subjective perception of an uncomfortable response to harmful stimulus to the body. Even when the diagnoses of the causes of the pain are identical, the perception of pain among different subjects can be quite different in terms of intensity and type of feeling. Pain is, therefore, an individual and subjective phenomena. For this reason, the quantification of the level of pain being experienced by an individual has been quite difficult.

However, it can definitely be said that pain can manifest at varying levels of distinguishable intensity that are related to the type and severity of the harmful stimuli. The perception of pain is, however, an individual response that is related to the individual subject's nervous system.

Furthermore, the perception of pain also has a psychological component that can cause different subjects to report their pain in different ways. For example, factors such as the individual subject's willpower (or lack thereof) and determination to overcome their illness or injury can influence the way in which they perceive and report their pain.

Some people have what is referred to as a high pain tolerance and others a low pain tolerance. That is, higher levels of pain may be experienced by those individuals possessing a high pain tolerance before they are unable to function in a normal manner or are otherwise adversely affected. For those persons having a low tolerance for pain, lower levels of pain adversely affect them. Thus, the pain may be somewhat subjective or at least is relative to each patient.

Determining how much pain is experienced by a particular patient can be helpful in treating that patient. In one situation, a patient may be the subject of a therapy program to overcome an injury or disease. Determining how much pain a patient experiences during the course of the therapy may greatly aid the therapist in selecting the proper therapies to provide to the patient. For example, a patient who is recovering from a shoulder injury may be experiencing a certain level of pain at the beginning of a therapy program. As the therapy proceeds, it would be helpful to the therapist to know if the pain is decreasing thereby indicating that the therapy is successful or at least is not aggravating the injury. However, if the level of pain does not decrease over time, or if it increases, knowledge of this could also aid the therapist in selecting other programs for the patient or in referring the patient back to a physician for further diagnosis.

In another situation, a patient may experience "soft tissue" injury. That is, no physical damage to the patient's body is apparent either visibly, by x-ray, or by other means yet the patient complains of pain. A therapy program may also be prescribed for this patient. Unfortunately, the program would be based upon the patient's expression of the level and location of his pain. It would be beneficial to have an objective measure for such a patient's pain level so the effects of any therapy program could be more accurately determined.

Therapies may be prescribed for such patients and are based only on the patient's input as to where the pain is in his body and under what conditions it worsens or lessens. In this case, there are no independent means to diagnosis the progress of the therapy other than the patient's subjective opinion that the pain is decreasing or increasing. It would be helpful to the therapist and physician to have a more objective indication of the level of pain experienced by the patient.

In a related circumstance to "soft tissue" and other pain, it has been found that in some cases a patient may complain of extreme pain when little or none is actually experienced. The reasons for doing so vary and may include pecuniary gain or an attempt to avoid further work. It would be helpful to be able to more objectively and more accurately test such a patient for the actual existence of pain.

Hence those skilled in the art have recognized the need for an improved pain measurement system and method capable of more accurately quantifying the amount of pain experienced by a patient. A further need has been recognized for a system and method that are able to more accurately determine if pain actually exists in a patient. The present invention fulfills these needs and others.

SUMMARY OF THE INVENTION

Briefly, and in general terms, the present invention is directed to a pain measurement system and method for providing a more objective measurement of the level of pain experienced by a patient.

In one aspect of the invention, a system for measuring the magnitude of pain experienced by a patient includes a contact adapted to be applied to a patient to deliver a tactile stimulus; an energy source connected to the contact to provide a controllable magnitude of tactile stimulus to the patient through the contact; a processor connected to the energy source to control the magnitude of tactile stimulus applied to the patient; and an indicator switch connected to the processor and adapted to be activated to provide a tactile indication signal to the processor that a magnitude of tactile stimulus has been experienced by the patient.

The processor is adapted to receive a first tactile indication signal, determine the first magnitude of tactile stimulus applied to the patient at the time of receipt of the first tactile indication signal, and store the first magnitude of tactile stimulus. The processor is further adapted to receive a second tactile indication signal, determine the second magnitude of tactile stimulus applied to the patient at the time of receipt of the second tactile indication signal, and compare the second magnitude of tactile stimulus to the first magnitude of tactile stimulus and provide a comparison signal.

In another aspect of the invention, a system for measuring the magnitude of pain experienced by a patient includes a contact adapted to be applied to a patient to deliver a pseudo-pain stimulus; an energy source connected to the contact to provide a controllable magnitude of pseudo-pain stimulus to the patient through the contact; a processor connected to the energy source to control the magnitude of pseudo-pain stimulus applied to the patient; and an indicator switch connected to the processor and adapted to be activated to provide a pseudo-pain indication signal to the processor that a magnitude of pseudo-pain has been experienced by the patient.

The processor is adapted to receive a first pseudo-pain indication signal, determine the first magnitude of pseudo-pain stimulus applied to the patient at the time of receipt of the first pseudo-pain indication signal, and store the first magnitude of pseudo-pain stimulus. The processor is further adapted to receive a second pseudo-pain indication signal, determine the second magnitude of pseudo-pain stimulus applied to the patient at the time of receipt of the second pseudo-pain indication signal, and compare the second magnitude of pseudo-pain stimulus to the first magnitude of pseudo-pain stimulus and provide a comparison signal.

The indicator switch is adapted to be activated by the patient to provide a pseudo-pain indication signal to the processor that a magnitude of pseudo-pain has been experienced by the patient. The contact can include an electrode adapted to deliver electric energy to the patient. The energy source provides energy to the contact with a steadily increasing magnitude until receipt by the processor of a pseudo-pain indication signal at which time the processor controls the energy source to cease delivery of electric energy to the contact.

The system preferably includes a display and a memory. The processor provides the comparison to the display to be displayed thereon. The processor also provides the comparison to the memory to be stored. The processor is adapted to store multiple comparison signals in the memory and to provide multiple stored comparison signals simultaneously to the display for display thereon.

The pseudo-pain stimulus signal can be a current of steadily increasing amperage, and may include a voltage having a duty cycle of less than 100 percent. The stimulus signal can be a voltage signal having a frequency of approximately 50 Hertz.

In yet another aspect of the invention, the system includes an electrode adapted to be applied to a patient to deliver an electric stimulus signal; an energy source connected to the electrode to provide the electric stimulus signal, the energy source capable of controlling the magnitude of the electric stimulus signal; a processor connected to the energy source to control the magnitude of the electric stimulus signal applied to the patient; a display; a memory; and a pseudo-pain indicator switch connected to the processor and adapted to be activated by the patient to provide a pseudo-pain indication signal to the processor that a magnitude of pseudo-pain has been experienced by the patient.

Generally, the processor receives a first pseudo-pain indication signal, determines the first magnitude of stimulus applied to the patient by the energy source at the time of receipt of the first pseudo-pain indication signal, and stores the first magnitude of stimulus in the memory. The processor receives a second pseudo-pain indication signal, determines the second magnitude of stimulus applied to the patient by the energy source at the time of receipt of the second pseudo-pain indication signal, compares the second magnitude of stimulus to the first magnitude of stimulus, and provides a comparison signal.

Preferably, the processor provides a first steadily increasing stimulus signal to the patient and upon receipt of the first pseudo-pain indication signal, the processor controls the energy source to cease delivery of energy to the electrode, and the processor stores the first magnitude of stimulus as a sensation threshold signal. The processor then provides a second steadily increasing stimulus signal to the patient and upon receipt of the second pseudo-pain indication signal, the processor controls the energy source to cease delivery of energy to the electrode, and the processor divides the second stimulus signal by the first stimulus signal to provide the comparison signal. The comparison signal can then be provided to the display for display thereon.

The pseudo-pain stimulus signal can be a current of steadily increasing amperage, and may include a voltage having a duty cycle of less than 100 percent. The stimulus signal can be a voltage signal having a frequency of approximately 50 Hertz. The stimulus signal can be a current of steadily increasing amperage. The processor is preferably adapted to store multiple comparisons in the memory and to provide multiple stored comparison signals to the display for display thereon.

In a still further aspect of the invention, a system for measuring the magnitude of pain experienced by a patient includes a contact adapted to be applied to a patient to deliver a pain stimulus; an energy source connected to the contact to provide a controllable magnitude of pain stimulus to the patient through the contact; a processor connected to the energy source to control the magnitude of pain stimulus applied to the patient; and an indicator switch connected to the processor and adapted to be activated to provide a pain indication signal to the processor that a magnitude of pain stimulus has been experienced by the patient.

The processor is adapted to receive a first pain indication signal, determine the first magnitude of pain stimulus applied to the patient at the time of receipt of the first pain indication signal, and store the first magnitude of pain stimulus. The processor is further adapted to receive a second pain indication signal, determine the second magnitude of pain stimulus applied to the patient at the time of receipt of the second pain indication signal, and compare the second magnitude of pain stimulus to the first magnitude of pain stimulus and provide a comparison signal.

In another aspect of the invention, a method for measuring the magnitude of pain experienced by a patient includes the steps of applying an electrode to a patient; applying an electric stimulus to the patient via the electrode; measuring the magnitude of the electric stimulus; applying an electric stimulus of an increasing magnitude to the patient via the electrode; monitoring a signal from the patient to determine when the first magnitude of the applied electric stimulus corresponds to a patient condition; and recording the first magnitude of the applied electric stimulus that corresponds to the patient condition.

In another aspect, the method further includes the step of recording at a subsequent time a second magnitude of the applied electric stimulus that corresponds to the patient condition. The method preferably further includes the step of comparing the first magnitude of the applied electric stimulus that corresponds to the patient condition to the second magnitude of the applied electric stimulus that corresponds to the patient condition.

These and other aspects of the invention will become apparent from the following detailed description and the accompanying drawings, which illustrate by way of example the features of the invention.

BRIEF DESCRIPTION OF THE DRAWINGS

FIG. 8 also presents an enlarged view of the bar chart of FIG. 7.

DETAILED DESCRIPTION OF THE PREFERRED EMBODIMENTS

In accordance with aspects of the invention, the system and method of the present invention make possible a more objective quantitative measurement of clinical pain. In general terms, the perception of the constant or preexisting pain [f(x)] generated by a subject's source of pain [x] is compared with a pseudo pain feeling [f(y)] that is produced by a gradual change in the electric simulation [y] generated by the system and provided to the subject. This system and method measure the point [y] at which the subject's perception of his preexisting pain [f(x)] approximates the intensity of the pseudo pain feeling [f(y)] generated by the system. In this way, the level of his source of pain [x] is estimated quantitatively.

Additionally, when there is a perception of pain that changes over time [f(x1)–f(xn)] generated by the subject's source of pain that changes over time [x1–xn], this system makes it possible to track and compare this over time with a changing pseudo pain feeling that also changes over time [f(y1)–f(yn)]. This system measures and tracks the points [y1–yn] at which the subject's perceptions of pain [f(x1)–f(xn)] approximate the intensity levels of the pseudo pain feelings [f(y1)–f(yn)] generated by the system. In this way, the changing levels of the source of pain [x1–xn] are estimated quantitatively and tracked over time.

Figure 1:
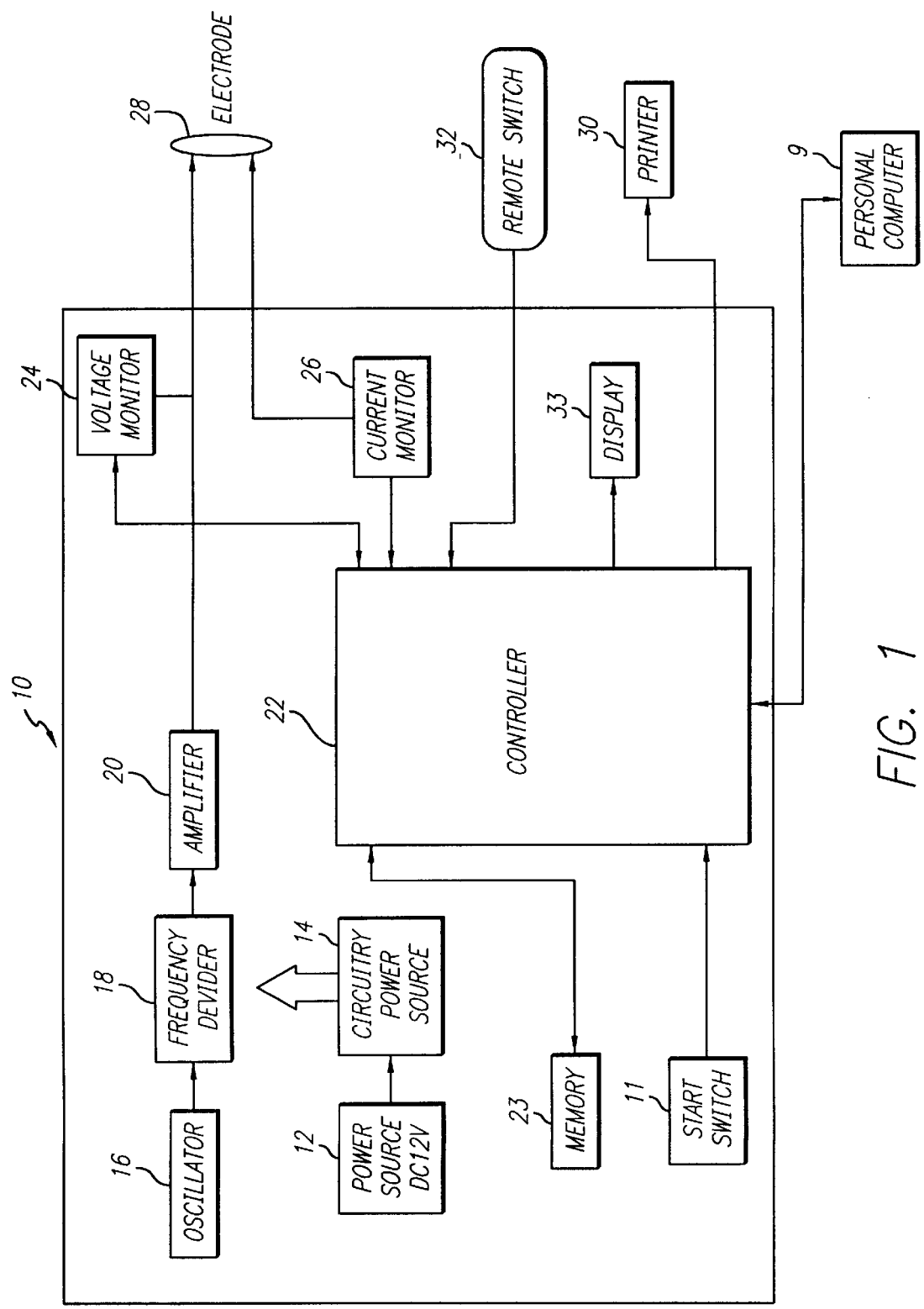
FIG. 1 is a schematic block diagram of the system embodying features of the invention.
Figure 2:
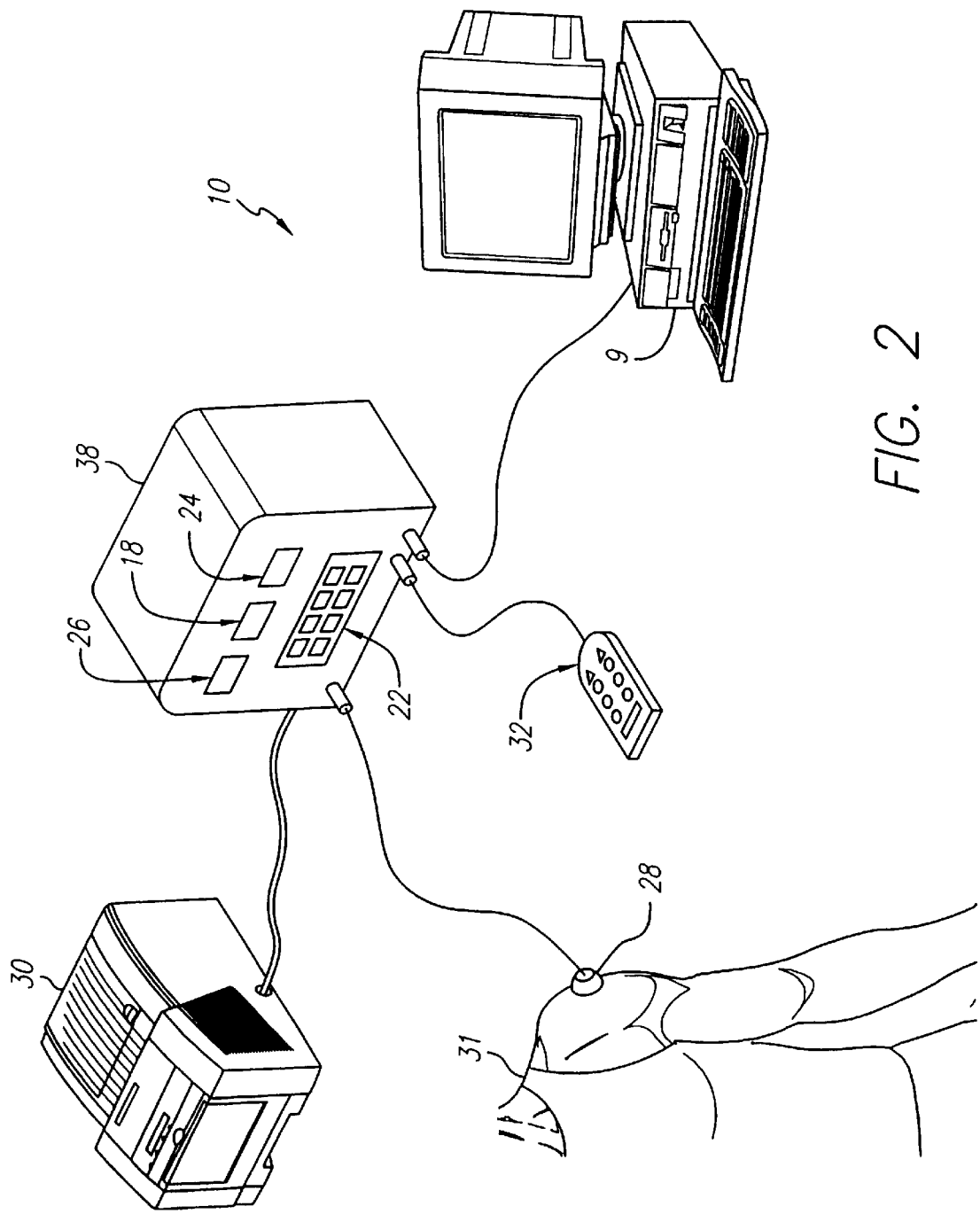
FIG. 2 is a perspective view of the system of FIG. 1 attached to a patient.

Referring now to the drawings wherein like reference numerals designate like or corresponding elements among the several views, FIGS. 1 and 2 present a presently preferred pain measurement system 10. The pain measurement system preferably includes a processor, such as a personal computer 9 and a controller 22. The pain measurement system also preferably includes a start switch 11, a 12 volt DC power source 12, a circuitry power source 14, an oscillator 16, a frequency divider 18, an amplifier 20, a memory 23, a voltage monitor 24, a current monitor 26, a contact such as an electrode 28, a printer 30, an indicator switch 32, and a display 33 connected to the controller 22. Certain elements may or may not be present depending on the desired configuration. For example, a printer 30 may not be necessary at all times. A personal computer 9 may not be necessary if its functions are contained in the controller 22.

The combination of the circuitry power source 14, the oscillator 16, the frequency divider 18, and the amplifier 20 provide an energy source connected to the contact or electrode 28. The energy source provides a stimulus the magnitude of which is controllable as is discussed below. The stimulus provided in this embodiment is electrical and because it is applied to the skin of the patient, it is termed a tactile stimulus.

The controller 22 provides two main functions: control over the rate and the amplitude of a stimulus that is applied to the subject and data manipulation and storage. The controller controls the rate at which the magnitude of a tactile stimulus, in this case an electric stimulus, is increased as well as takes measurements, including starting, stopping, and resetting, recording measurements, comparing measurements, and providing appropriate display and print signals, as applicable. The controller can be attached to the personal computer 9, which can aid in performing necessary calculations.

Referring now in more detail to FIGS. 1 and 2, an operator first activates the system 10 via the start switch 11 which is connected to the controller 22. The controller used may be any suitable controller, such as a controller commonly found in a personal computer. The electric stimulus signal is generated by the oscillator 16 and the frequency divider 18. The 12 volt DC power source 12 preferably includes one or more batteries; however, any suitable 12 volt DC power source may be used with the present system. The 12 volt DC power source is used to power the circuitry power source 14, which in turn powers the frequency divider and may include any suitable circuitry capable of converting the 12 volt DC power in an appropriate manner. The circuitry power source contains a 100 V step-up transformer in one embodiment. An AC to DC adapter may also be used as the power source 14 to convert wall power, such as 120 VAC, to 12 VDC. The electric stimulus signal is fed from the frequency divider to the amplifier 20, whereupon the signal is amplified and applied to the electrode 28. The magnitude of amplification rate of change of amplification and duty cycle are controlled by the controller.

A subject or patient who feels a certain magnitude of pain [y1] in response to the severity of a preexisting condition causing the pain [x1] will also experience a certain magnitude of sensation [y2] in response to an external tactile stimulus [x2] applied by the system 10 through the electrode 28. The voltage monitor 24 and current monitor 26 are used to read the voltage and current, respectively, that are applied to the electrode. The controller 22 is programmed to control the amplifier 20 to apply an increasing voltage to the electrode and thereby provide an increasing current to the patient. The voltage monitor and current monitor are used to determine the actual voltage and current applied to the patient. Their values at the time the indicator switch 32 (which is located remotely) is activated by the patient are stored by the controller in memory 23.

As the controller 22 increases the signal stimulus [x2], the intensity of the resultant sensation [y2] increases in the patient. The patient determines the point at which the intensity of the sensation [y2] caused by the electrical stimulus [x2] approximates the intensity of the pain [y1] caused by the original condition causing the preexisting pain [x1], and activates the indicator switch 32 when this point is reached. This switch 32 activation provides a tactile indication signal to the controller. In the embodiment shown and described herein, an electrical signal is provided to the patient to cause pseudo-pain. Therefore, the indication signal caused by activation of the switch 32 may also be known as a pseudo-pain indication signal. The tactile indication signal caused by the numerical value [x2] of the applied stimulus, such as the current, at this point can be stored in the memory 23, displayed on the display 33, and printed on the printer 30, and is used to quantify the intensity of the patient's pain [x1]. In order to account for personal differences in different subject's responses to electric stimuli, the value assigned to the patient's pain level [x2] is based on a value obtained by forming a ratio with the subject's minimum perception level, which is the level at which the subject first reports a sensation in response to the gradually applied external stimulus. A measurement to determine the subject's minimum perception level is normally performed before the actual pain measurement test.

Figure 4:
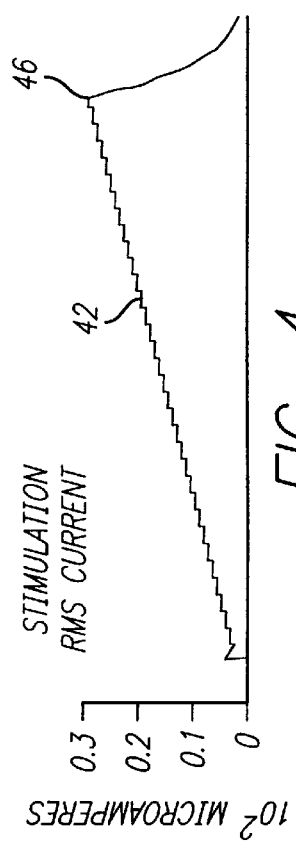
FIG. 4 is a line graph depicting the applied stimulus RMS current increasing in a substantially linear fashion as a function of time.
Figure 3:
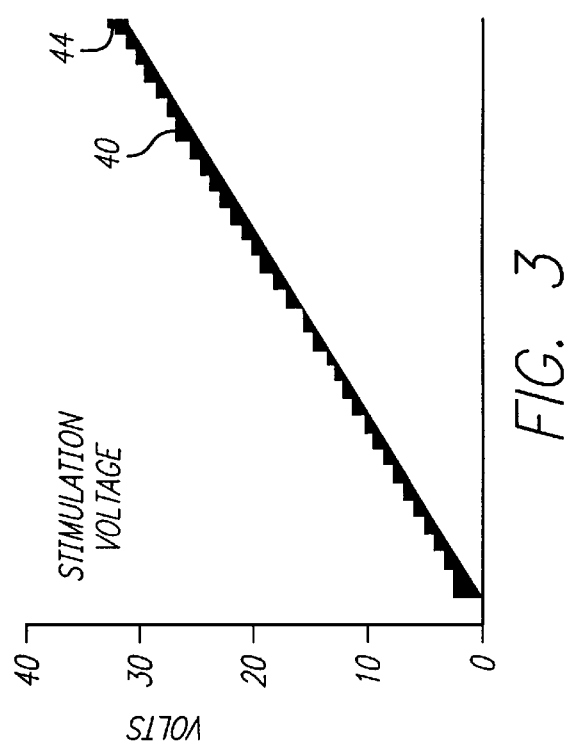
FIG. 3 is a line graph depicting the applied stimulus voltage increasing in a substantially linear fashion as a function of time.

Referring to FIGS. 3 and 4, voltage and current graphs are shown that have been used in the system shown in FIG. 1. As the voltage 40 to the patient 31 is increased by the controller 22, the current 42 also increases. In this embodiment, a voltage limiter is used and will not permit the voltage to exceed a predetermined maximum level 44 such as 100 volts. Likewise, a current limiter prevents the current from exceeding a predetermined maximum level 46. As is shown in FIG. 3, in this embodiment the voltage is automatically increased at a predetermined rate, or slope, by the controller 22. It has been found that the selection of the rate of voltage increase can affect the test results. For example, a voltage that rises too fast does not permit the patient enough time to activate the indicator switch 32 before the voltage and current levels have significantly changed. A rate that is too slow will result in a test that is too long. One embodiment used a rate of voltage increase of between 30 and 40 seconds approximately for the voltage starting at zero to reach its maximum level of 100 volts.

Figure 5:
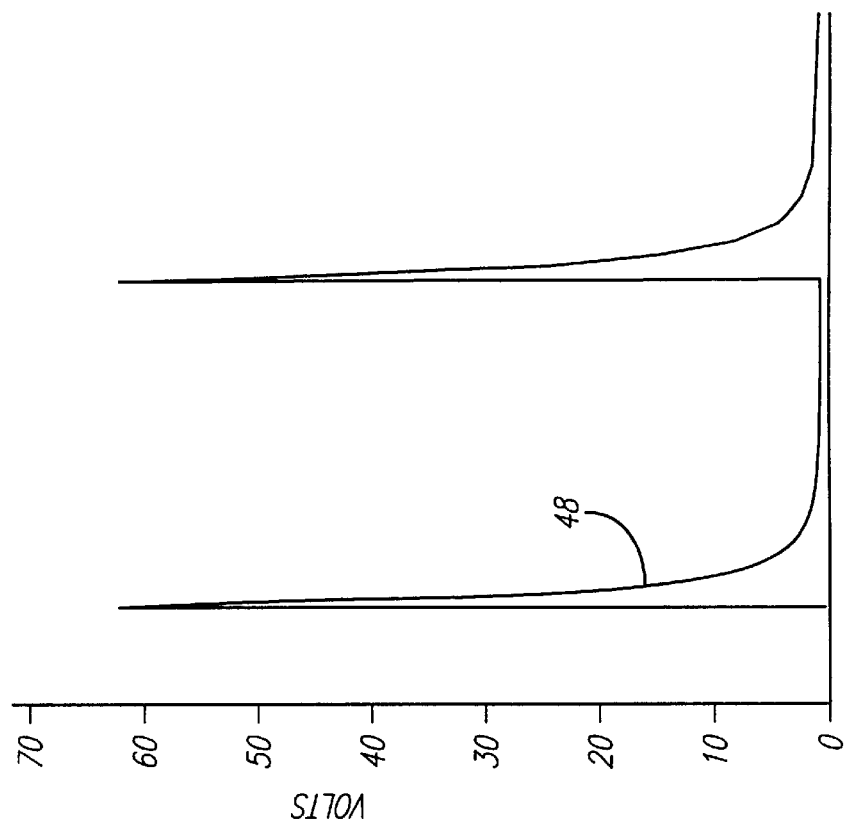
FIG. 5 is a line graph depicting a 1 millisecond voltage pulse width, showing an amplitude of approximately 65 volts and a duty cycle of approximately 10 percent.

Referring now to FIG. 5, a voltage waveform 48 used in one embodiment is shown. The system 10 produces an electric stimulus (one form of tactile stimuli) signal that has a one-millisecond voltage pulse width and a 50 Hertz frequency at a 5 percent duty cycle. It has been found that this pulse width frequency and duty cycle approximate a square wave and do not cause pain to patients yet do provide a suitable and clear sensory stimulation. This stimulation is referred to as a "pseudo-pain" stimulation.

FIG. 4 shows the root-mean-square (RMS) current as a function of time, and varies between 0 and $0.3 \times 10^2$ microamperes. One purpose of selecting the duty cycle to be less than 100 percent and the frequency to be approximately 50 Hertz is to provide a stimulus signal that the patient clearly experiences as a tangible, but non-painful sensation. That signal is gradually increased from zero for two general purposes in accordance with the present embodiment. The first is to determine a minimum perception level of the patient. That is, the current level at which the patient first senses the electrical stimulation provided by the system 10. That current level is stored in memory 23 and will be used in ratios later. The second is to determine the current level applied to the patient at which the patient feels that the pseudo-pain equals his actual pain. The current at this perceived equality of pseudo-pain with actual pain is stored and used in a comparison as discussed below. When the patient feels that the magnitudes of the actual pain and pseudo-pain caused by the electric stimulus are the same, he stops the stimulus via an indicator switch 32. The value of the current of the stimulus at which the subject stopped the electric stimulus corresponds to the magnitude of the electric stimulus and is used in a ratio as an index of the pain of the patient.

In consideration of the contact impedance of the skin and the electrodes, the position of the measuring point, and differences among individuals in their perception of pain, a "pain ratio" is used. The pain ratio is defined as the ratio of the current level of the pseudo-pain that the patient judged to be equivalent to the level of actual pain being experienced to the current level at which the subject is first able to sense the electric stimulus, i.e., the minimum perception level.

In this embodiment, measured values are obtained making use of the subject's reporting of his own sensations. In this regard, the system of the embodiment is similar to standard tests used to quantitatively measure vision and hearing, which also rely upon the subject reporting his responses to stimuli generated by the measurement system. In this embodiment, the pain equivalence current level is compared to the minimum perception level by the processor and a comparison signal is produced. That comparison signal is a pain ratio and is displayed and/or printed as described below.

Figure 6:
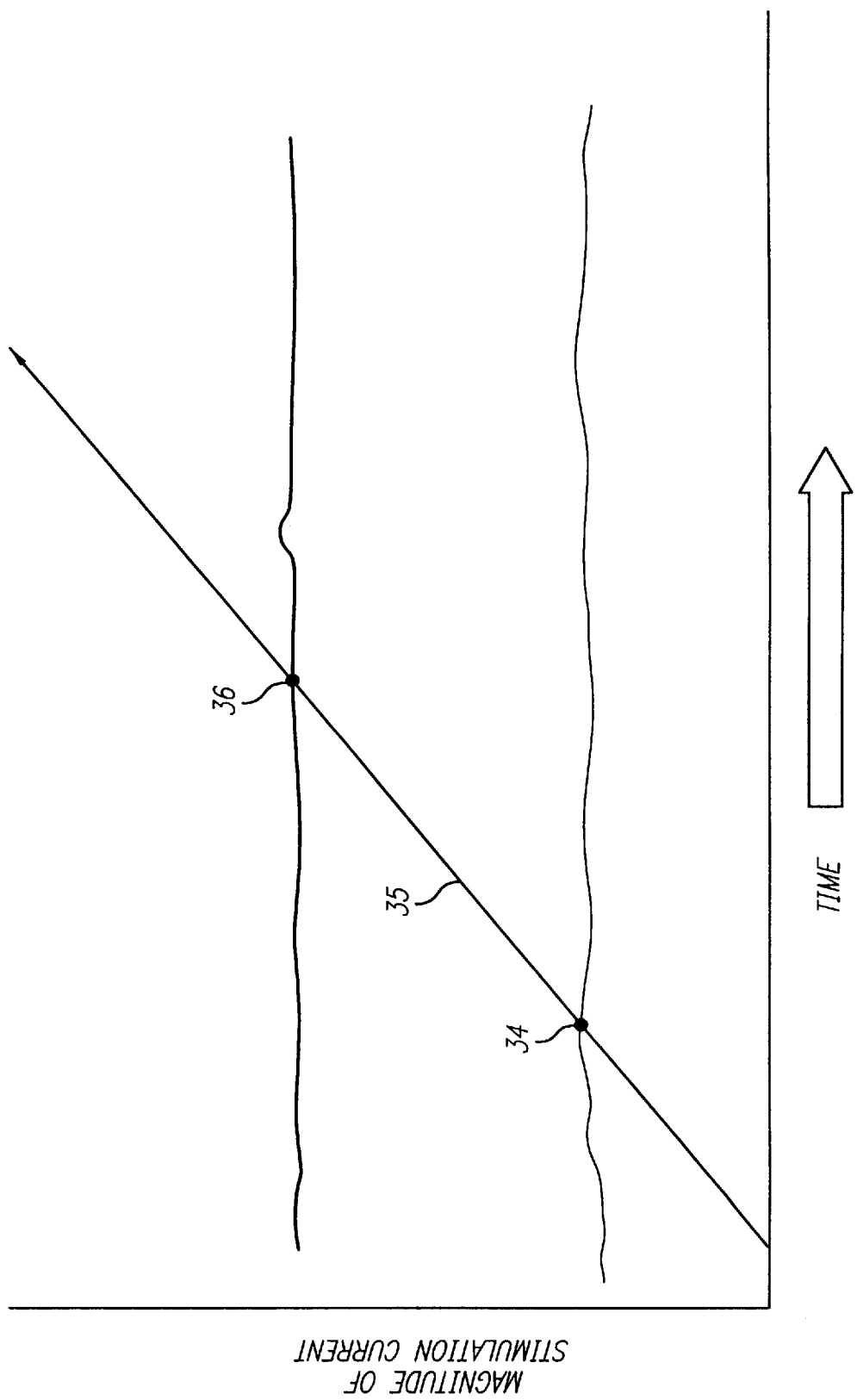
FIG. 6 is a line graph depicting electric stimulus current as a function of time crossing the minimum perception level of the subject and the pain equivalence level of that subject.

FIG. 6 is a graphical representation of both the minimum perception level and the equivalence perception level. Although the electrical stimulus 35 is shown in FIG. 6 as a single line, the minimum perception level 34 and equivalence perception level 36 are typically measured separately. The current level of the tactile stimulus is recorded as the minimum perception level and provides the denominator of the pain ratio. Following the measurement of the minimum perception level, the electric tactile stimulus is provided to the patient and he is asked to indicate via the indicator switch 32 when the magnitude of the tactile stimulus equals the magnitude of his preexisting pain. The current level 36 of the tactile stimulus existing at the time the patient activates the remote switch provides the numerator of the pain ratio. The quotient of the pain ratio quantitatively corresponds to the preexisting pain level of the patient.

Multiple measurements of the pain equivalence current level may be made to obtain an average reading. It has been found that for subjects experiencing relatively constant pain levels, the multiple pain equivalence measurements will be relatively close. The average will be near each reading. For those patients experiencing pain that comes and goes, or for those patients experiencing no pain, the measurements vary widely.

Conventional clinical electrodes 28 for low frequency medical treatment devices are preferably employed in the system of the present invention. It is preferable to apply the electrode to a point that does not produce muscular contraction.

The system and method disclosed above were used on numerous subjects and repeatable results were obtained.

Studies showed that the measurement value of the minimum perception current could be influenced by the incrementation speed of the loading current. If a current incrementation speed of $0.10 \times 10^2$ microamperes per second is maintained, however, sufficient reproducibility is provided.

Figure 7:
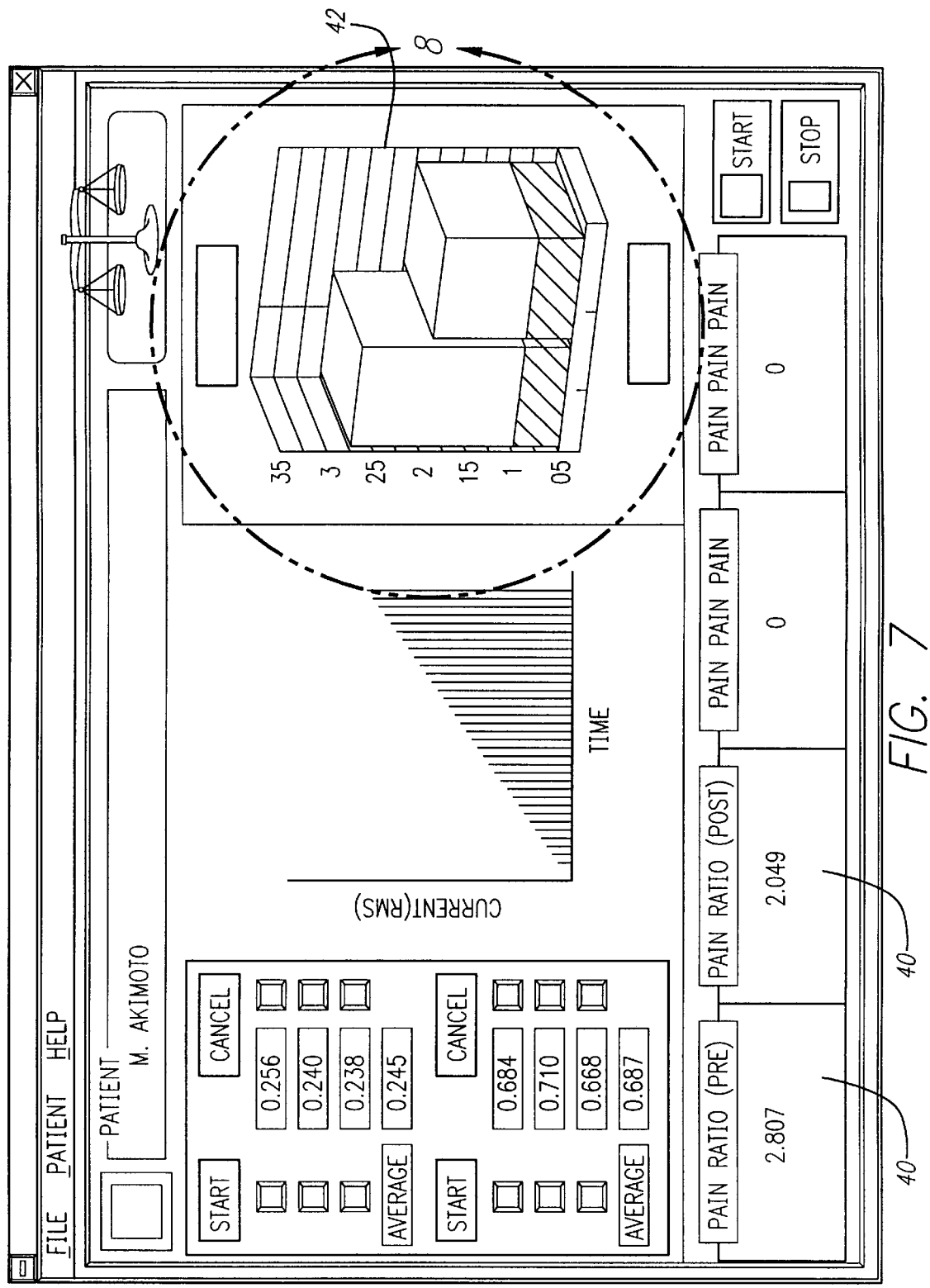
FIG. 7 is a front view of a graphical user interface for communicating with the system according to aspects of the present invention.
Figure 8:
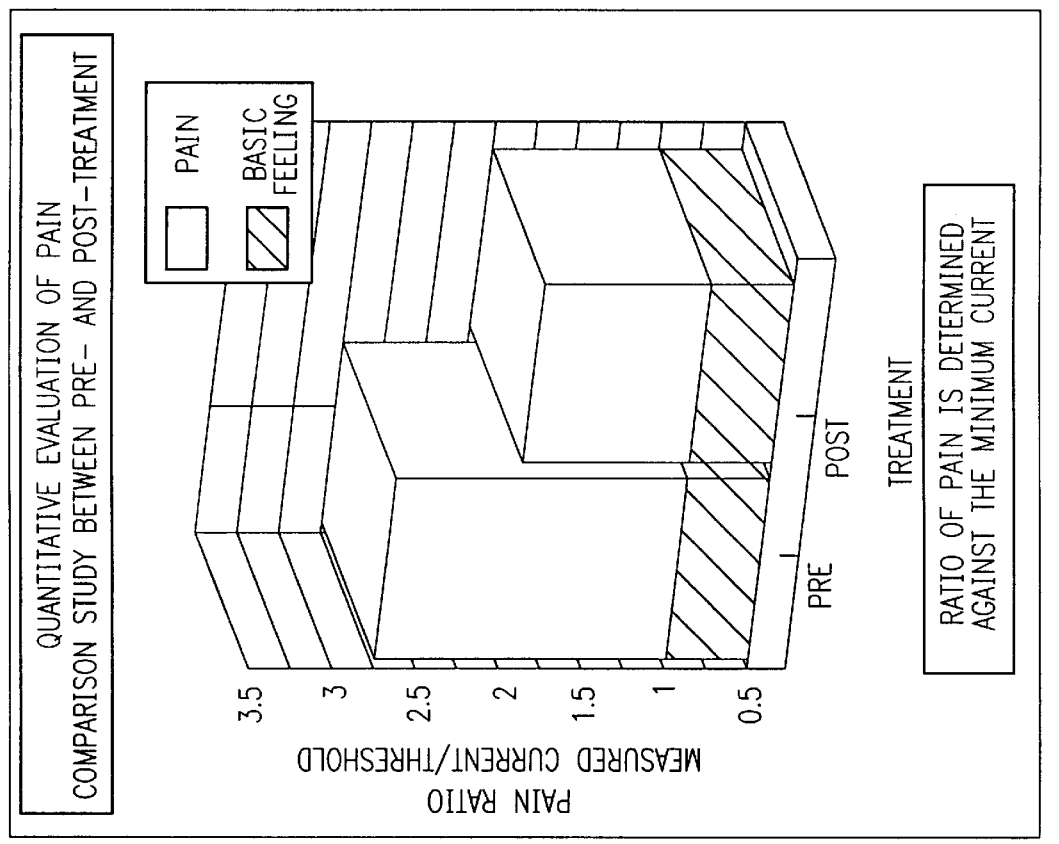
FIG. 8 is a different graphical user interface that includes pre and post therapy pain measurements, comments, and a bar graph depicting the ratio of the measured value of electric stimulus current corresponding to a patient condition to the measured threshold value of current.

While a separate personal computer 9 is shown as being used in FIG. 2, alternatively the computer may be integrated into the housing 38. In the figures shown and described below, the program used was compatible with Microsoft Windows 95 and presented a graphical format, as depicted in FIG. 7. The comparison signal (i.e. pain ratio) from the processor is displayed as a numerical output 40 in this embodiment. Not only are numerical outputs 40 provided, but also graphical bar charts 42 may be provided, as desired. As shown in FIG. 8, the bar charts may illustrate calculated pain ratios for both pre-therapy and post-therapy measurements. In this way, one may easily see if there has been a change in the magnitude of pain that the subject is experiencing. A printed record may also be made. Other embodiments of the data output are possible.

In the output screen shown in FIG. 7, the subject is identified by name at the top. Two sets of pain equivalence current measurements are presented at the left side. Each set of three current measurements is followed by an average. At the bottom left of the screen, it becomes apparent that one set of three current measurements represents the subject's pain level pre-therapy and the second set of three measurements represents the subject's pain level post-therapy. The numbers 40 at the bottom left of the screen (2.807 and 2.049) are the quotients from the actual ratios of the average actual pain current to the current for the minimum perception level, which was measured previously.

FIG. 8 presents an interface screen presenting somewhat different information. At the left of the screen, the minimum perception current ("threshold of electric current") as shown for pre-therapy and for post-therapy. The actual pain current levels are also shown. The pain ratios are presented and below the ratios, comments may be entered about the subject, the test, or other things. In the case shown in FIG. 8, three minimum perception level measurements were performed.

An electrode is applied to the patient 60 and an electric stimulus is applied 62. If the minimum perception level of the patient has not been determined 64, the controller monitors a signal from the patient 66. If the patient provides the signal 68, the magnitude of the stimulus is monitored 70 and is stored 72. If the minimum perception level had already been measured at decision box 64, the signal from the patient is monitored 74, and when received 76, the magnitude of the stimulus is measured as the equivalence perception level 78. The value is stored 80 and compared to the minimum perception level 82. The result may be displayed 84 and or printed. If another measurement is desired 89, the stimulus is reset and the process repeated 86.

Figure 9:
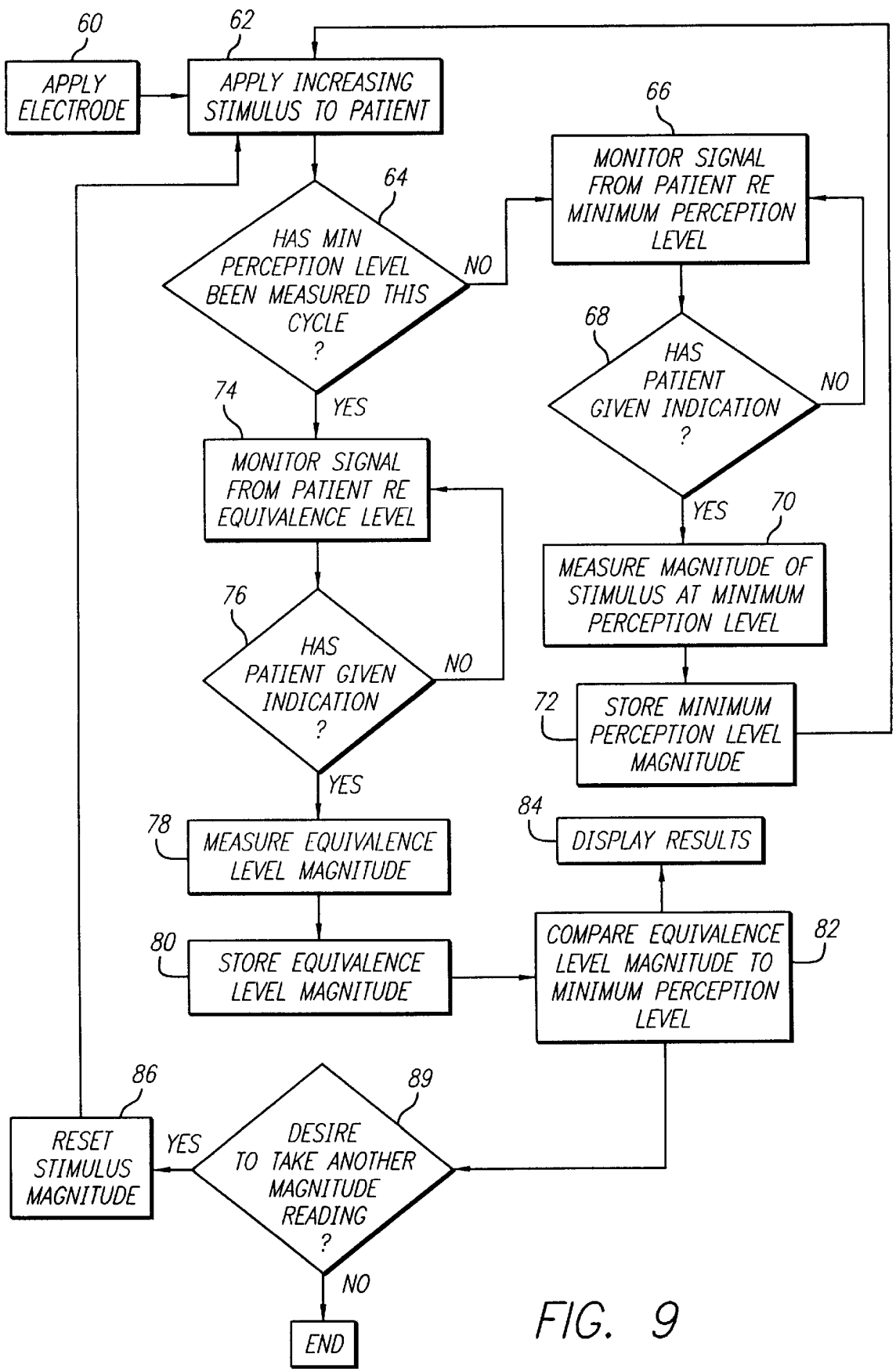
FIG. 9 is a flow chart depicting one preferred method in accordance with the present invention.

FIG. 9 illustrates one preferred method of the present invention, as discussed supra, wherein a first magnitude of applied electric stimulus that corresponds to the patient's condition is recorded, and at a later time a second magnitude of applied electric stimulus that corresponds to the patient's condition may be recorded. Subsequent recordings of magnitude may also be made.

The usefulness of the system in quantitatively measuring constant pain was validated experimentally using an artificially applied experimental reference pain on 56 student volunteers (27 male and 29 female). The measurement of the stimulus current was obtained for both the minimum perception current and the pain equivalence current. Experimental reference pain was generated by means of a compression plate (2 cm diameter) applied to the subject's forearm at an applied pressure of 100–200 mmHg.

The usefulness of the system in tracking and quantifying levels of pain that change over time was also validated, using women experiencing labor pains as their time for giving birth approached. It is believed therefore that this invention has great potential as a medical device used for quantitatively measuring both constant and fluctuating clinical pain.

It was determined that, regardless of whether or not pain was present, the minimum perception current did not change for each subject. It was shown that, although the nature of the sensations of the experimental reference pain and the stimulus current were different, the subjects were still able to evaluate when the two levels were equivalent with a high degree of reproducibility.

A linear relationship was shown wherein an increase of magnitude of electric stimulus corresponded to an increase of magnitude of pressure applied for the experimental reference pain. A great increase of the speed of the magnitude of the applied stimulus current had a slight impact on the pain equivalency current magnitudes reported, but when the speed was increased within an established range there was no impact on the measurement results. In the embodiment shown and described above, the rate of change of the voltage applied to the subject was fixed. In another embodiment, provision may be made to allow for the operator to vary the rate of changes as desired.

Although the tactile stimulus described above was an electric stimulus, the concepts are generally applicable to other stimuli as well, such as actual pain stimuli, mechanical stimuli, heat stimuli, and chemical stimuli. The above description has been generally confined to an electric stimulus in consideration of avoiding unnecessary repetition. Should an actual pain stimulus indication signal would now be known as a pain indication signal. Furthermore, measurement cycles have been shown and described herein as consisting of three measurements. It has been found that taking three measurements increases reliability, increases accuracy, and makes it more difficult for a subject to take pain. However, more or fewer measurements may be taken as desired. Additionally, three minimum perception level measurements were sown as being taken. This amount may also vary.

With the system and method shown and described above, a physician or other user may determine the amount of painkiller to prescribe to a patient, may track the success of rehabilitation efforts, and determine more objectively the amount of pain a subject is experiencing. Other uses are likely possible. Because a ratio is used, the patient's individual characteristics (minimum perception level) as to pain perception are neutralized and a more objective pain quantification is made. As is apparent, this approach has many benefits in more objectively monitoring the pain of subjects.

It will be apparent from the foregoing that while particular forms of the invention have been illustrated and described, various modifications can be made without departing from the spirit and scope of the invention. Accordingly, it is not intended that the invention be limited, except as by the appended claims,

What is claimed is:

1. A system for measuring the magnitude of pain experienced by a subject, comprising:

a contact adapted to be applied to a subject to deliver a tactile stimulus;

an energy source connected to the contact to provide a controllable magnitude of tactile stimulus to the subject through the contact;

a processor connected to the energy source to control the magnitude of tactile stimulus applied to the subject;

an indicator switch connected to the processor and adapted to be activated to provide a tactile indication signal to the processor that a magnitude of tactile stimulus has been experienced by the subject;

wherein the processor is adapted to receive a first tactile indication signal, determine the first magnitude of tactile stimulus applied to the subject at the time of receipt of the first tactile indication signal, and store the first magnitude of tactile stimulus; and wherein the processor is further adapted to receive a second tactile indication signal, determine the second magnitude of tactile stimulus applied to the subject at the time of receipt of the second tactile indication signal, and compare the second magnitude of tactile stimulus to the first magnitude of tactile stimulus and provide a comparison signal.

2. A system for measuring the magnitude of pain experienced by a subject, comprising:

a contact adapted to be applied to a subject to deliver a pseudo-pain stimulus;

an energy source connected to the contact to provide a controllable magnitude of pseudo-pain stimulus to the subject through the contact;

a processor connected to the energy source to control the magnitude of pseudo-pain stimulus applied to the subject;

an indicator switch connected to the processor and adapted to be activated to provide a pseudo-pain indication signal to the processor that a magnitude of pseudo-pain has been experienced by the subject;

wherein the processor is adapted to receive a first pseudo-pain indication signal, determine the first magnitude of pseudo-pain stimulus applied to the subject at the time of receipt of the first pseudo-pain indication signal, and store the first magnitude of pseudo-pain stimulus; and wherein the processor is further adapted to receive a second pseudo-pain indication signal, determine the second magnitude of pseudo-pain stimulus applied to the subject at the time of receipt of the second pseudo-pain indication signal, and compare the second magnitude of pseudo-pain stimulus to the first magnitude of pseudo-pain stimulus and provide a comparison signal.

3. The system of claim 2, wherein the indicator switch is adapted to be activated by the subject to provide a pseudo-pain indication signal to the processor that a magnitude of pseudo-pain has been experienced by the subject.

4. The system of claim 2, wherein the contact comprises an electrode adapted to deliver electric energy to the subject.

5. The system of claim 2, wherein the energy source provides energy to the contact with a steadily increasing magnitude until receipt by the processor of a pseudo-pain indication signal at which time the processor controls the energy source to cease delivery of electric energy to the contact.

6. The system of claim 2, further comprising a display, wherein the processor provides the comparison to the display to be displayed thereon.

7. The system of claim 2, further comprising a memory, wherein the processor provides the comparison to the memory to be stored.

8. The system of claim 7, further comprising a display, wherein the processor is adapted to provide the comparison signal to the display for display thereon.

9. The system of claim 8, wherein the processor is adapted to store multiple comparison signals in the memory and to provide multiple stored comparison signals simultaneously to the display for display thereon.

10. The system of claim 2, wherein the pseudo-pain stimulus signal comprises a current of steadily increasing amperage.

11. The system of claim 2, wherein the pseudo-pain stimulus signal comprises a voltage having a duty cycle of less than 100 percent.

12. The system of claim 2, wherein the stimulus signal comprises a voltage signal having a frequency of approximately 50 Hertz.

13. A system for measuring the magnitude of preexisting pain experienced by a subject, comprising:

an electrode adapted to be applied to a subject to deliver an electric stimulus signal;

an energy source connected to the electrode to provide the electric stimulus signal, the energy source capable of controlling the magnitude of the electric stimulus signal;

a processor connected to the energy source to control the magnitude of the electric stimulus signal applied to the subject;

a display;

a memory;

a pseudo-pain indicator switch connected to the processor and adapted to be activated by the subject to provide a pseudo-pain indication signal to the processor that a magnitude of pseudo-pain has been experienced by the subject;

wherein the processor receives a first pseudo-pain indication signal, determines the first magnitude of stimulus applied to the subject by the energy source at the time of receipt of the first pseudo-pain indication signal, and stores the first magnitude of stimulus in the memory;

wherein the processor receives a second pseudo-pain indication signal, determines the second magnitude of stimulus applied to the subject by the energy source at the time of receipt of the second pseudo-pain indication signal, compares the second magnitude of stimulus to the first magnitude of stimulus, and provides a comparison signal; and wherein the processor provides the comparison signal to the display for display thereon.

14. The system of claim 13, wherein the processor provides a first steadily increasing stimulus signal to the subject and upon receipt of the first pseudo-pain indication signal, stores the first magnitude of stimulus as a sensation threshold signal;

wherein the processor provides a second steadily increasing stimulus signal to the subject and upon receipt of the second pseudo-pain indication signal, divides the second stimulus signal by the first stimulus signal to provide the comparison signal;

wherein the processor provides the comparison signal to the display for display thereon.

15. The system of claim 13, wherein the stimulus signal comprises a current of steadily increasing amperage.

16. The system of claim 13, wherein the stimulus signal comprises a voltage having a duty cycle of less than 100 percent.

17. The system of claim 13, wherein the stimulus signal comprises a voltage signal having a frequency of approximately 50 Hertz.

18. The system of claim 13, wherein the energy source provides electric energy to the electrode in a steadily increasing magnitude until receipt by the processor of a pseudo-pain indication signal at which time the processor controls the energy source to cease delivery of energy to the electrode.

19. The system of claim 13, wherein the processor is adapted to store multiple comparisons in the memory and to provide multiple stored comparison signals to the display for display thereon.

20. A system for measuring the magnitude of pain experienced by a subject, comprising:

a contact adapted to be applied to a subject to deliver a pain stimulus;

an energy source connected to the contact to provide a controllable magnitude of pain stimulus to the subject through the contact;

a processor connected to the energy source to control the magnitude of pain stimulus applied to the subject;

an indicator switch connected to the processor and adapted to be activated to provide a pain indication signal to the processor that a magnitude of pain stimulus has been experienced by the subject;

wherein the processor is adapted to receive a first pain indication signal, determine the first magnitude of pain stimulus applied to the subject at the time of receipt of the first pain indication signal, and store the first magnitude of pain stimulus; and wherein the processor is further adapted to receive a second pain indication signal, determine the second magnitude of pain stimulus applied to the subject at the time of receipt of the second pain indication signal, and compare the second magnitude of pain stimulus to the first magnitude of pain stimulus and provide a comparison signal.

21. A method for measuring the magnitude of pain experienced by a subject, comprising the steps of:

applying an electric stimulus of an increasing magnitude to the subject via an electrode;

measuring the magnitude of the electric stimulus;

monitoring a signal from the subject to determine when the first magnitude of the applied electric stimulus corresponds to a first subject condition; and recording the first magnitude of the applied electric stimulus that corresponds to the subject condition;

monitoring a signal from the subject at a second time to determine when the second magnitude of the applied electric stimulus corresponds to a second subjects condition;

comparing the second magnitude to the first magnitude.

* * * * *